United States Patent [19]
Lim

[11] Patent Number: 5,709,787
[45] Date of Patent: Jan. 20, 1998

[54] WIDE-RANGE AIR FUEL RATIO OXYGEN SENSOR

[75] Inventor: Chang-bin Lim, Seoul, Rep. of Korea

[73] Assignee: Samsung Electro-Mechanics Co., Ltd., Kyungki-do, Rep. of Korea

[21] Appl. No.: 535,916

[22] Filed: Sep. 28, 1995

[30] Foreign Application Priority Data

Sep. 30, 1994 [KR] Rep. of Korea ............. 94-25202

[51] Int. Cl.$^6$ ............................................. G01N 27/27
[52] U.S. Cl. ................... 204/425; 204/426; 204/427; 204/429; 422/83
[58] Field of Search ........................... 204/425, 426, 204/427, 428, 429; 422/83

[56] References Cited

U.S. PATENT DOCUMENTS

| | | | |
|---|---|---|---|
| 3,514,377 | 5/1970 | Spacil et al. | 204/195 S X |
| 3,981,785 | 9/1976 | Sandler | 204/195 S |
| 4,132,615 | 1/1979 | Linder et al. | 204/195 S |
| 4,502,939 | 3/1985 | Holfelder et al. | 204/429 |
| 4,505,807 | 3/1985 | Yamada | 204/425 |
| 4,841,934 | 6/1989 | Logothetis et al. | 123/440 |
| 4,902,400 | 2/1990 | Usami et al. | 204/426 |
| 5,074,987 | 12/1991 | Thompson | 204/410 |
| 5,271,816 | 12/1993 | Tanaka et al. | 204/153.16 |

*Primary Examiner*—Harold Y. Pyon
*Attorney, Agent, or Firm*—Foley & Lardner

[57] ABSTRACT

A wide-range air fuel ratio oxygen sensor including a pump cell, a sensor cell, and a porous diffusion layer interposed between the pump cell and the sensor cell and a method for fabricating the oxygen sensor. The oxygen sensor generates output pumping current with a very small dispersion range of about ±2% by virtue of the activation effect of the catalyst such as Pt mixed into $Al_2O_3$ of the porous diffusion layer.

8 Claims, 3 Drawing Sheets

1

WIDE-RANGE AIR FUEL RATIO OXYGEN SENSOR

BACKGROUND OF THE INVENTION

1. Field of the Invention

The present invention relates to an air fuel ratio oxygen sensor and a method for fabricating the same, and more particularly to a wide-range air fuel ratio oxygen sensor made of an oxygen ion-transmitting solid electrolyte and provided with a porous diffusion layer in which a catalyst is distributed and a method for fabricating the same.

2. Description of the Prior Art

For the purpose of a purification of exhaust gas and an improvement in fuel consumption ratio in vehicles, detection of the concentration of oxygen contained in exhaust gas from an engine is carried out. Conventionally, such a detection has been achieved using λ type gas sensors and limit current type sensors, which are made of a solid electrolyte wherein a charge transfer in a solid body is generally achieved by ions. However, the λ type gas sensors have disadvantages of a small variation in electromotive force and a low sensitivity obtained at an excessively thick oxygen region. On the other hand, the limit current type sensors are improper to detect air fuel ratios in a wide range and difficult to ensure a good quality under mass production. In order to overcome these problems encountered in both the λ type gas sensor and the limit current type sensor, there has been proposed an oxygen sensor constructed by a combination of the λ type gas sensor and the limit current type sensor and adapted to detect air fuel ratios in a full range. This composite type oxygen sensor includes the combination of a sensor cell and a pump cell both made of an oxygen ion-transmitting solid electrolyte. The oxygen sensor has a porous diffusion structure having diffusion path as gas inlet to receive exhaust gas. As current flowing in the pump cell is controlled by a constant electromotive force from the sensor cell, the output current is linearly varied depending on the air fuel ratio. On the basis of such a principle, there has been proposed a sensor adapted to sense air fuel ratios in a full range from output pumping current and known as "wide-range air fuel ratio oxygen sensor". This sensor has a porous oxide layer interposed between its sensor cell and pump cell to achieve a diffusion of exhaust gas in a fashion similar to that of the limit current type sensor. Such a wide-range air fuel ratio oxygen sensor is employed in exhaust gas analyzers as well as fuel controllers of vehicles.

Conventional wide-range air fuel ratio oxygen sensors generate output pumping current with a dispersion of more than ±5% in the fuel-rich region. For this reason, they include a circuit for compensating the wide dispersion range of output pumping current. However, the provision of such a compensating circuit results in a complex sensing circuit and an unreasonably expensive sensor construction. Such a wide scattering of output pumping current has been known as being caused by a difficulty of a uniform introduction of exhaust gas because of a severe scattering phenomenon occurring at diffusion pores serving as exhaust gas inlet. Actually, exhaust gas contains a large amount of unburned gas under nonequilibrium condition. This unburned gas is considered as adversely affecting performances of the sensor cell and pump cell.

SUMMARY OF THE INVENTION

Therefore, an object of the invention is to provide a wide-range air fuel ratio oxygen sensor including a porous diffusion layer made of a catalyst-distributed oxide, capable of changing components of exhaust gas of nonequilibrium condition, in particular, three primary gases, namely, CO, $H_2$ and HC into those of equilibrium condition by the porous diffusion layer, thereby inhibiting an increase in resistance caused by non-uniform reaction of oxygen in its diffusion chamber, that is, on cathode surfaces of its sensor cell and pump cell in and a local oxygen consumption, and capable of ionizing oxygen before it reaches the electrodes, thereby achieving a reduction in the gas diffusion resistance caused by absorption and desorption of oxygen occurring at electrode interfaces, and thereby capable of generating output pumping current with a narrow scattering range.

Another object of the invention is to provide a method for fabricating the wide-range air fuel ratio oxygen sensor.

In accordance with one aspect, the present invention provides a wide-range air fuel ratio oxygen sensor comprising a pump cell, a sensor cell, and a porous diffusion layer interposed between the pump cell and the sensor cell, wherein a catalyst is distributed in the porous diffusion layer.

In accordance with another aspect, the present invention provides a method for fabricating a wide-range air fuel ratio oxygen sensor comprising a pump cell, a sensor cell, and a porous diffusion layer interposed between the pump cell and the sensor cell, comprising the steps of: mixing $Al_2O_3$ with a metal chloride acid solution containing a catalyst, thereby producing catalyst-distributed $Al_2O_3$ powder; forming a porous diffusion layer made of the catalyst-distributed $Al_2O_3$ powder between the pump cell and the sensor cell, thereby forming a multilayer structure; and co-firing the multilayer structure.

BRIEF DESCRIPTION OF THE DRAWINGS

Other objects and aspects of the invention will become apparent from the following description of embodiments with reference to the accompanying drawings in which.

DETAILED DESCRIPTION OF THE PREFERRED EMBODIMENTS

Figure 1:
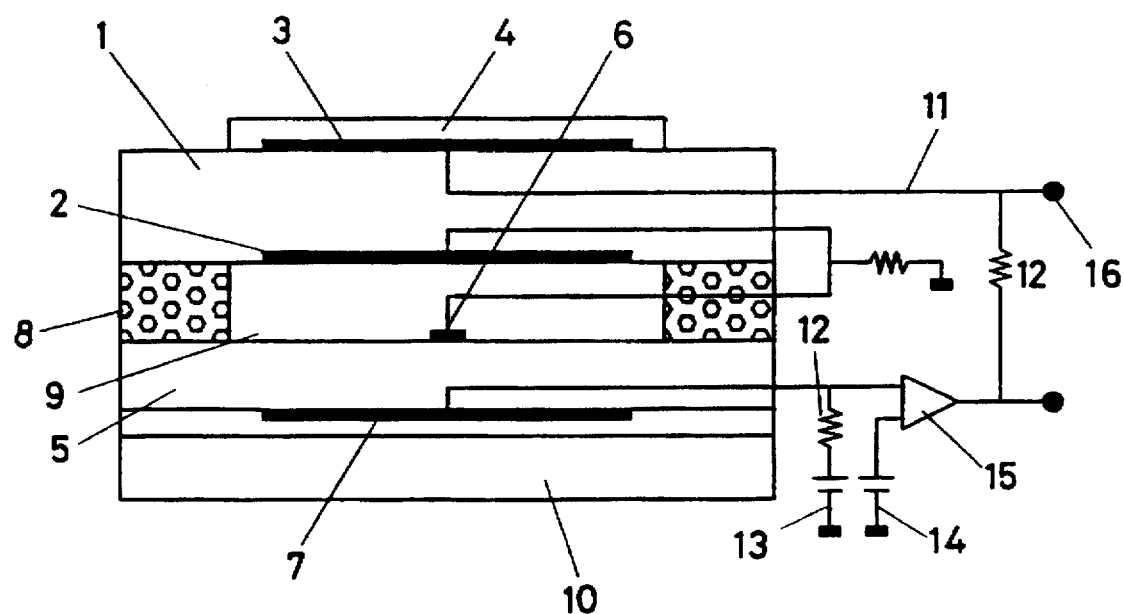
FIG. 1 is a view illustrating a wide-range air fuel ratio oxygen sensor fabricated in accordance with the present invention.

FIG. 1 is a view illustrating a wide-range air fuel ratio oxygen sensor fabricated in accordance with an embodiment of the present invention.

As shown in FIG. 1, the wide-range air fuel ratio oxygen sensor of the present invention has a multilayer structure including a pump cell 1, a sensor cell 5 (oxygen detecting cell) and a substrate 10. Each of the layers 1, 5, 10 is comprised of a green sheet made of a $ZrO_2$ oxide containing a solid solution of $Y_2O_3$ in an amount of 6 to 8 mols. The green sheet has a thickness of 0.6 to 0.8 mm, a width of 5 to 7 mm, and a length of 20 to 25 mm and is fabricated using a doctor blade method. The pump cell 1 is provided at its opposite surfaces respectively with a pair of Ip electrodes 2 and 3. Each of the Ip electrodes 2 and 3 is formed by coating a Pt paste layer, having a width of 1.8 to 2 mm and a length of 4 to 5 mm, on each corresponding surface of the pump cell 1. On the other hand, the sensor cell 5 is provided at its opposite surfaces respectively with a pair of Vs electrodes 6 and 7. Each of the Vs electrodes 6 and 7 is formed by coating a Pt paste layer, having a width of 1 to 1.2 mm, a length of 4 to 5 mm and a thickness of 10 to 20 μm, on each corresponding surface of the sensor cell 5. The positive (+) Ip electrode 3 is coated with a porous layer 4 for electrode protection. The porous layer 4 is formed by coating $Al_2O_3$ over the Ip electrode 3 to a thickness of 10 μm. A catalyst-distributed porous diffusion layer 8 is interposed between the pump cell 1 and the sensor cell 5. The porous diffusion layer 8 is formed by mixing $Al_2O_3$ with a small amount of YSZ powder having the same composition as the pump cell 1, blending the mixture into a metal chloride acid solution such as $H_2PtCl_6 \cdot nH_2O$ in a ratio that the content of the metal, for example, Pt is 0.1 to 5 wt % based on $Al_2O_3$, thereby producing a paste, and then coating the paste on the pump cell 1. At a dried state of the paste, an organic solvent may be used. When the paste contains the metal in an amount less than 0.1 wt %, a desired effect expected by the addition of the metal can not be obtained. The metal content exceeding 5 wt % results in a degradation in characteristic. In place of Pt, other metals may be used as the metal component of the metal chloride acid for obtaining the desired effect in accordance with the present invention. These metals may include a noble metal such as Pd or Rh, a transition metal such as Cu, Ni, Mn, Cr or Co, or a rare-earth metal such as $Sm_2O_3$.

The paste is coated to a thickness of 100 to 200 μm on the lower surface of pump cell 1 formed with the negative (−) Ip electrode 2 under a condition that it does not cover the Ip electrode 2, thereby forming the porous diffusion layer 8. Thereafter, the sensor cell 5 is layered on the pump cell 1 with the porous diffusion layer 8 such that its negative Vs electrode 6 faces the negative Ip electrode 2 of the pump cell 1. As a result, a diffusion chamber 9 is defined by the porous diffusion layer 8 between the pump cell 1 and the sensor cell 5. The positive (+) Vs electrode 7 provided at the lower surface of sensor cell 5 is coated with a electrode protection layer made of a mixture of $ZrO_2$ and $Al_2O_3$. The electrode protection layer is also used to bond the substrate 10 to the sensor cell 5. After bonding the pump cell 1, sensor cell 5 and substrate 10 together, the resulting multilayer structure is subjected to a co-firing at a temperature of 1,400° to 1,600° C. for an appropriate time. At this time, the co-firing should be appropriately controlled in a fashion that the porosity and pore size of the porous diffusion layer 8 are appropriately adjusted. Where the porous diffusion layer 8 has pores with a very small size, it may involve a phenomenon that the pores are chocked by impurities contained in exhaust gas during the use of the sensor and thereby causing a degradation in durability and reproductivity.

The electrodes of the pump cell 1 and sensor cell 5 are electrically connected, by means of lead wires 11, to an electric circuit including resistors 12, a comparator 15, an Icp source 13 and a sensor cell reference voltage source 14. With such a construction, it is possible to detect an output pumping current flowing between opposite terminals of the electric circuit, namely, the positive Ip electrode 3 and the comparator 15.

Operation of the oxygen sensor fabricated in the above-mentioned manner in accordance with the present invention will now be described.

As shown in FIG. 1, the wide-range air fuel ratio oxygen sensor is constituted by three planar $ZrO_2$ solid electrolyte sheets and provided at the interior thereof with the catalyst-distributed porous diffusion layer 8 and the diffusion chamber 9. That is, the $ZrO_2$ solid electrolyte sheets constitute the substrate 10, the oxygen pumping cell (Ip cell) 1 and the sensor cell (Vs cell) 5 for generating a reference voltage, respectively. Pt electrodes are screen-printed on opposite surfaces of the pump cell 1 and opposite surfaces of the sensor cell 5, respectively. The substrate 10 is adapted to provide an oxygen reference electrode and generally known as "Icp cell". As microcurrent from the Icp source 13 flows in the sensor cell 5, oxygen is pumped by the oxygen pumping cell 1. As current flows in the Vs cell, namely, the sensor cell 5 by the Icp source 13, oxygen is pumped. Once the oxygen reference electrode, namely, the positive Vs electrode 7 is filled with oxygen by the oxygen pumping operation, an electromotive force (Vs voltage) is generated by virtue of the difference between partial oxygen pressures at the opposite sides of the sensor cell 5. As the pumping current Ip is controlled such that the electromotive force obtained by the partial oxygen pressure difference is maintained at 450 mV, the Ip cell, namely, the oxygen pumping cell performs its pumping operation. Thus, the partial oxygen pressure in the diffusion chamber (gas detecting chamber) 9 can be controlled. In this case, the output pumping current value (namely, output Ip) has the value corresponding to the air fuel ratio to be measured. Therefore, the air fuel ratio of an object exhaust gas can be measured by detecting the output pumping current. However, such an output pumping current value has a tolerance of ±5% in the fuel-rich region. For this reason, a circuit for compensating such a tolerance has been conventionally needed. The tolerance of output pumping current value may be resulted from a local reaction of oxygen occurring during gas under nonequilibrium condition acts chemical reaction, absorption and desorption on cathode surfaces of the pump cell and sensor cell in the diffusion chamber, or resulted from a diffusion resistance caused by the absorption and desorption of $O_2$ carried out on electrode interfaces. However, the sensor in accordance with the present invention eliminates the use of the compensating circuit because the diffusion chamber is formed by the Pt-distributed porous diffusion layer between the pump cell and the sensor cell. The Pt-distributed porous diffusion layer serves to promote the following reactions carried out in the diffusion chamber:

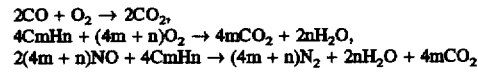
$2CO + O_2 \rightarrow 2CO_2$,
$4C_mH_n + (4m + n)O_2 \rightarrow 4mCO_2 + 2nH_2O$,
$2(4m + n)NO + 4C_mH_n \rightarrow (4m + n)N_2 + 2nH_2O + 4mCO_2$ As a result, gas in the diffusion chamber is changed from the nonequilibrium state to the equilibrium state and then supplied at the cathode side. Accordingly, it is possible to inhibit a local chemical reaction of the gas on the electrodes. Furthermore, oxygen is ionized before it reaches the electrodes, by virtue of the function of catalyst, thereby achieving a reduction in diffusion resistance. By referring to FIG. 3, it can be found that output pumping current with the dispersion range of ±2% is obtained. Thus, the sensor in accordance with the present invention eliminates the use of the compensating circuit.

The present invention will be understood more readily with reference to the following examples including a single example in accordance with the present invention and a single comparative example in accordance with the prior art; however these examples are intended to illustrate the invention and are not to be construed to limit the scope of the present invention.

EXAMPLE 1

For preparing a pump cell 1, a sensor cell 5 and a substrate 10, green sheets having a thickness of 0.6 to 0.8 mm, a width of 5 to 7 mm, and a length of 20 to 25 mm were fabricated using a doctor blade method. Each of the green sheet was made of a $ZrO_2$ oxide containing a solid solution of $Y_2O_3$ in an amount of 6 to 8 mols. Thereafter, Ip electrodes 2 and 3 were formed respectively at opposite surfaces of the green sheet for the pump cell 1 by coating a Pt paste layer, having a width of 1.8 mm, a length of 5 mm and a thickness of 15 µm, on the surfaces of the green sheet. Vs electrodes 6 and 7 were formed respectively at opposite surfaces of the green sheet for the sensor cell 5 by coating a Pt paste layer, having a width of 1.2 mm, a length of 5 mm and a thickness of 15 µm, on the surfaces of the green sheet. The positive (+) Ip electrode 3 were then coated with a porous layer 4 for electrode protection. The porous layer 4 were formed by coating $Al_2O_3$ over the Ip electrode 3 to a thickness of 10 µm. Thereafter, a catalyst-distributed porous diffusion layer 8 was formed on the pump cell 1. The porous diffusion layer 8 was formed by mixing $Al_2O_3$ with 2 wt % YSZ powder, blending the mixture into $H_2PtCl_6 \cdot nH_2O$ in a ratio that the content of Pt is about 3 wt % based on $Al_2O_3$, thereby producing a paste, and then coating the paste on the pump cell 1 without covering the negative Ip electrode. The sensor cell 5 was then bonded to the pump cell 1 by means of an adhesive, thereby forming a diffusion chamber 9 defined by the porous diffusion layer 8 between the pump cell 1 and the sensor cell 5. Subsequently, the positive Vs electrode 7 provided at the lower surface of sensor cell 5 was coated with composite powder of $ZrO_2$ and $Al_2O_3$. Using the layer coated on the sensor cell 5, the substrate 10 was then bonded to the sensor cell 5. After completing the bonding, the resulting multilayer structure was subjected to a co-firing at a temperature of about 1,500° C. for about one hour. Finally, the electrodes of the pump cell 1 and sensor cell 5 were electrically connected, by means of lead wires 11, to an electric circuit including resistors 12, a comparator 15, an Icp source 13 and a sensor cell reference voltage source 14 so as to detect an output pumping current flowing between opposite terminals of the electric circuit, namely, the positive Ip electrode 3 and the comparator 15.

COMPARATIVE EXAMPLE 1

In this example, an oxygen sensor was fabricated using the same method as Example 1, except for elimination of the addition of the noble metal, Pt to its porous oxide layer.

Characteristics of both the oxygen sensors respectively fabricated in accordance with Example 1 and Comparative Example 1 were measured in accordance with the following method, in order to compare the effect of the catalyst-distributed porous diffusion layer in accordance with the present invention with that of the conventional one.

$O_2$ gas was mixed with an exhaust gas sample having a composition consisting of 100 to 600 ppm $C_3H_6$, 300 to 5,500 ppm NOx, 500 to 3,000 ppm CO, 100 to 500 ppm $H_2$, and the balance $N_2$ so as to obtain λ of 0.8 to 1.6 (namely, the air fuel ratio of 11 to 24). The resulting gas mixture was heated at 700° C. The heated gas was then forced to pass through both the oxygen sensors respectively fabricated in accordance with Example 1 and Comparative Example 1 at a rate of 2,000 cc/min. Results generated at the oxygen sensors are shown in FIGS. 2 and 3, respectively.

Figure 2:
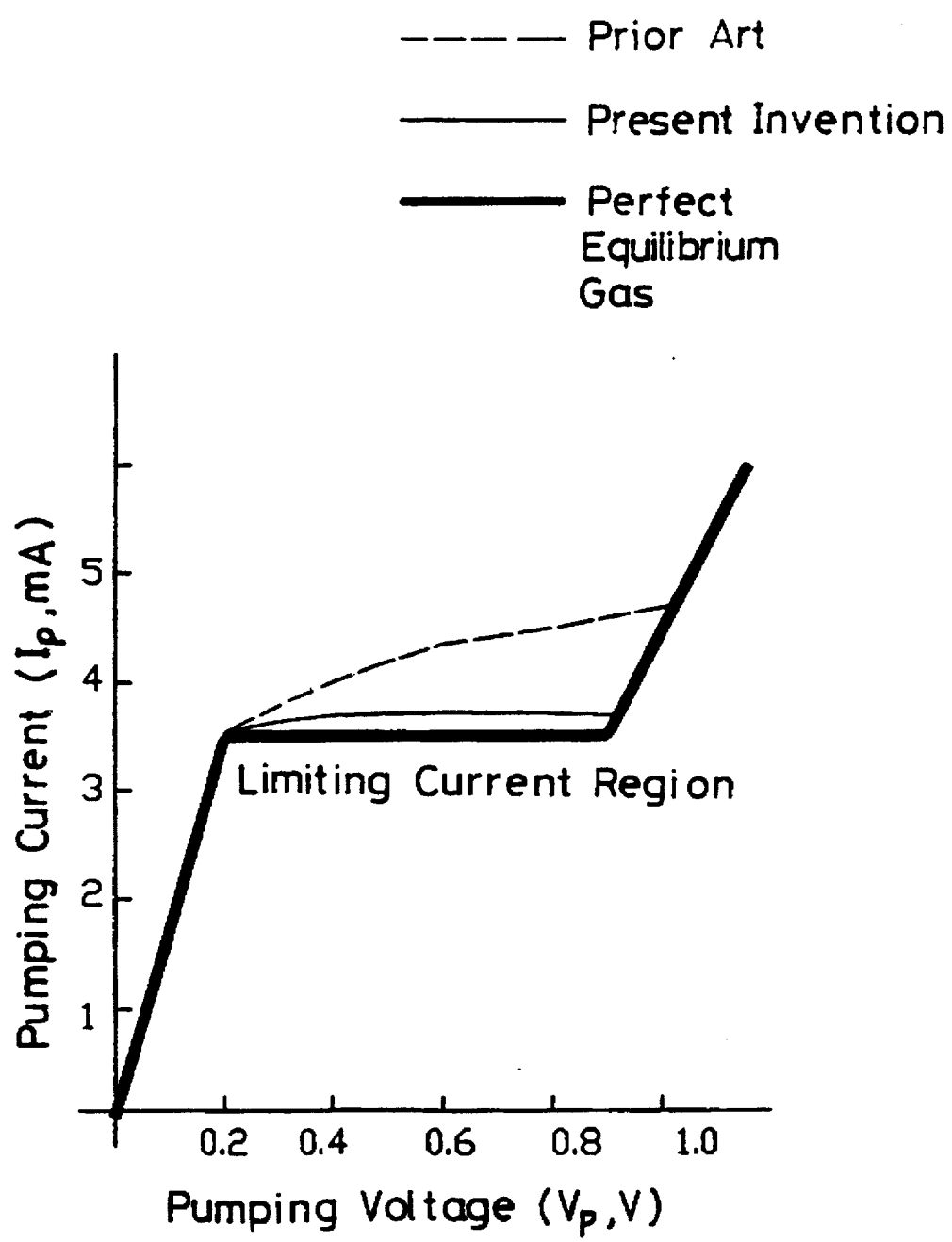
FIG. 2 is a graph showing an output pumping current characteristic of a wide-range air fuel ratio oxygen sensors depending on the pumping voltage.

FIG. 2 shows an output pumping current characteristic of the oxygen sensors depending on the pumping voltage (for the air fuel ratio of 10). On the other hand, FIG. 3 shows an output pumping current characteristic of the oxygen sensors depending on the air fuel ratio.

Figure 3:
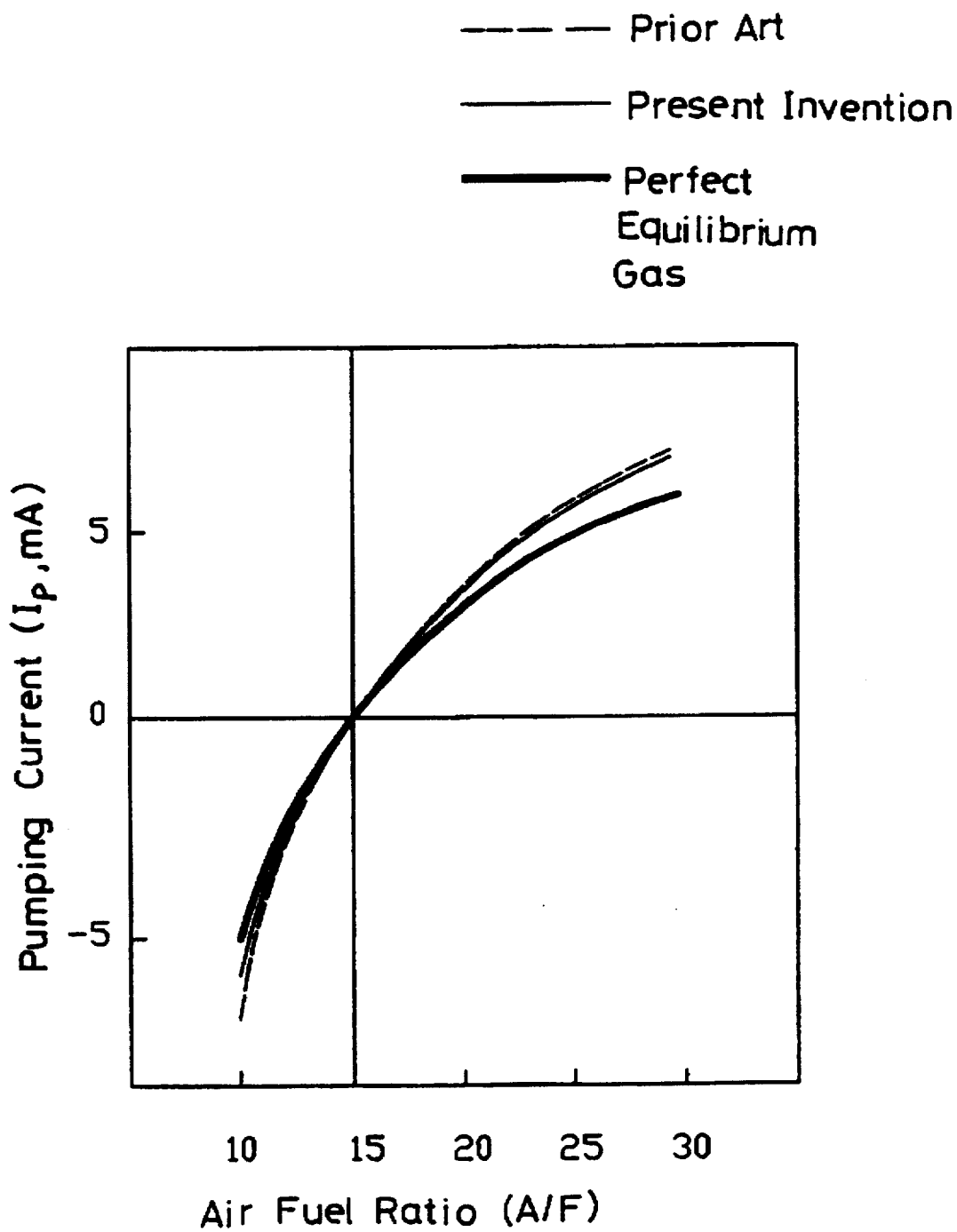
FIG. 3 is a graph showing an output pumping current characteristic of the oxygen sensors in accordance with the present invention depending on the air fuel ratio.

Referring to FIGS. 2 and 3, it can be found that the oxygen sensor of the present invention generates output pumping current with a very small dispersion range of about ±2% by virtue of the activation effect of Pt catalyst mixed into $Al_2O_3$ of the porous diffusion layer, even though the output pumping current has a value slightly lower than that of the conventional oxygen sensor. This means that the present invention makes it possible to obtain output current of the range not requiring any compensating circuit even at a thin oxygen region or an excessively thick oxygen region. Also, the dispersion range of output pumping current may be more narrowed through an improvement in the structure of porous diffusion layer.

As apparent from the above description, the present invention provides an oxygen sensor capable of reducing a local oxygen consumption at electrode interfaces of its sensor cell and pump cell in its diffusion chamber, reducing the gas diffusion resistance by virtue of the reduced local oxygen consumption, and reducing the electric resistance by virtue of a pre-ionization of $O_2$, thereby obtaining a good output pumping current characteristic with a dispersion range of ±2% at widely-ranged oxygen regions between a thin oxygen region and a thick oxygen region. Accordingly, the present invention eliminates use of any compensating circuit.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A wide-range air fuel ratio oxygen sensor comprising a pump cell, a sensor cell, and a porous diffusion layer interposed between the pump cell and the sensor cell, wherein a catalyst is distributed in the porous diffusion layer.

2. A wide-range air fuel ratio oxygen sensor in accordance with claim 1, wherein the catalyst is distributed in an amount of 0.1 to 5 wt % based on the weight of the porous diffusion layer.

3. A wide-range air fuel ratio oxygen sensor as claimed in claim 1, wherein the sensor is capable of generating an output pumping current with a dispersion range of ±2%.

4. A wide-range air fuel ratio oxygen sensor in accordance with claim 1, wherein the catalyst is a metal selected from a group consisting of Pt, Pd and Rh, which are noble metals, Cu, Ni, Mn, Cr and Co, which are transition metals, and $Sm_2O_3$ which is a rare-earth metal.

5. A wide-range air fuel ratio oxygen sensor in accordance with claim 4, wherein the catalyst is distributed in an amount of 0.1 to 5 wt % based on the weight of the porous diffusion layer.

6. A wide-range air fuel ratio oxygen sensor as claimed in claim 1, wherein the pump cell is provided at its opposite surfaces respectively with a pair of Ip electrodes, and wherein the sensor cell is provided at its opposite surfaces respectively with a pair of Vs electrodes.

7. A wide-range air fuel ratio oxygen sensor as claimed in claim 6, wherein the Ip electrodes and the Vs electrodes are formed by coating a Pt paste layer on each surface of the pump cell.

8. A wide-range air fuel ratio oxygen sensor as claimed in claim 6, further comprising a diffusion chamber defined by portions of the porous diffusion layer that do not cover the Ip or Vs electrodes disposed on the pump cell and sensor cell.

* * * * *